United States Patent [19]

Ellestad et al.

[11] 4,357,936
[45] Nov. 9, 1982

[54] DIRECTIONAL THERMISTOR ASSIST SENSING

[75] Inventors: Raymond A. Ellestad, Rialto; Finn Sveen, Redlands, both of Calif.

[73] Assignee: Bear Medical Systems, Inc., Calif.

[21] Appl. No.: 139,628

[22] Filed: Apr. 14, 1980

Related U.S. Application Data

[63] Continuation-in-part of Ser. No. 17,793, Mar. 5, 1979, abandoned.

[51] Int. Cl.³ .............................................. A61M 16/00
[52] U.S. Cl. ........................... 128/204.23; 128/724; 73/204; 340/606
[58] Field of Search ............... 128/204.21, 204.23, 128/204.26, 724; 73/204; 340/606

[56] References Cited

U.S. PATENT DOCUMENTS

| | | | |
|---|---|---|---|
| 3,368,212 | 2/1968 | Playce | 340/606 |
| 3,831,596 | 8/1974 | Cavallo | 128/204.23 |
| 3,896,800 | 7/1975 | Cibulka | 128/204.26 |
| 3,962,917 | 6/1976 | Terada | 128/724 |
| 3,972,327 | 8/1976 | Ernst et al. | 128/204.21 |
| 4,043,196 | 8/1977 | Trageser | 73/204 |
| 4,106,503 | 8/1978 | Rosenthal et al. | 128/203.12 |
| 4,141,356 | 2/1979 | Smargiassi | 128/204.23 |

FOREIGN PATENT DOCUMENTS

| | | | |
|---|---|---|---|
| 2317431 | 10/1974 | Fed. Rep. of Germany | 128/724 |
| 1279011 | 4/1952 | France | 128/204.26 |
| 584845 | 12/1977 | U.S.S.R. | 128/724 |

*Primary Examiner*—Henry J. Recla

[57] ABSTRACT

A directional sensor for the detection of a very feeble effort to breathe on the part of a patient whose breathing needs are under the influence and control of a mechanical ventilator. A self-heated thermistor assembly is mounted in a small diameter sensor tube. A diaphragm and chamber arrangement provides a low volume flow of air in the sensor tube past the thermistor assembly at a high velocity, so that a very small effort to breathe will draw a limited volume of air past the thermistor assembly at a high velocity, causing rapid cooling. The air will flow past the thermistor assembly in a first direction in response to an inhalation effort, and in a second direction in response to an exhalation effort. A heating element is arranged in the tube so that a first temperature-related voltage change is produced across the thermistor assembly when air flow is in the first direction, and a second such temperature-related voltage change is produced when air flow is in the second direction. The first voltage change resulting across the thermistor assembly is utilized to signal a patient effort to inhale and to command the ventilator to furnish an appropriate response, while the second voltage change, signaling an exhalation effort, is used to block such a response.

23 Claims, 10 Drawing Figures

WAVE FORMS

FIG. 8

DIRECTIONAL THERMISTOR ASSIST SENSING

CROSS REFERENCE TO RELATED APPLICATION

This is a Continuation-In-Part of co-pending Application Ser. No. 017,793; filed Mar. 5, 1979 now abandoned.

BACKGROUND OF THE INVENTION

1. Field of the Invention

This invention relates generally to mechanical ventilators and respiratory aids and more particularly to patient effort sensing means whereby the ventilator may be commanded to an appropriate operating mode.

2. Description of the Prior Art

While presently available respiratory systems can furnish operating modes of various parameter bases, it becomes important with very weak patients to sense an almost infinitesimal attempt to breathe. On the other hand, excessive pandering to the respiratory needs of the patient can build up a harmful addiction of the patient upon the ventilator such that the patient will be unable to breathe on his own even after he has physically recovered sufficiently to do so.

Modern respirators, therefore, have been developed in response to patient needs, and may thus operate in a number of modes among which is commonly included a control mode. In the control mode, a patient is totally dependent on the ventilator for his respiratory needs. That is to say, the ventilator completely controls all the respiratory functions of the patient including rate of breathing, volume of breathing gas to be inhaled by the patient, and all other rates and pressures permitted and furnished by the ventilator to the patient.

In another mode, the assist mode, in response to an initial effort by the patient to breathe, the ventilator "assists" the patient by delivering a predetermined breath to the patient. The breath so delivered is in all ways similar to the abovedescribed controlled breath except that the rate of breathing is determined by the patient himself in response to his efforts to breathe. In the pure assist mode, therefore, no breath is furnished to the patient until he makes an effort to breathe on his own. Stated in another way, if the patient does not attempt to breathe on his own, no breath will be furnished to him by the machine. It is thus of the utmost importance that every effort, no matter how feeble, that the patient makes to breathe be sensed. If the effort is not sensed, then no breath can be furnished to the patient as a result of his effort and he remains dependent upon the backup provisions, if any, of the ventilator. Thus his dependence upon the machine would become increased and his addiction thereto exacerbated.

Another mode of lesser interest in the instant invention is denominated the spontaneous mode. In the spontaneous mode the ventilator functions primarily to furnish blended breathing gas to the patient as required by him by maintaining a constant positive airway pressure (CPAP). In this mode, the patient must be strong enough to draw sufficient breathing gas into his body to constitute a complete breath. In the ventilator machine to be described as an exemplar for the purpose of explaining the instant invention, the spontaneous mode will have little, if any, application.

Although some prior art respirators have been satisfactory in their operation to a point, it has been found that they were lacking in sensitivity in some respects. The needs of some patients were thus not met under some conditions. For example, one patient may be able to initiate a stronger breathing impulse than another. If the weaker patient's effort is not sensed, however, the purpose of the assist mode is not being implemented in his case. It thus becomes important to mechanize as sensitive a system as possible in order to sense every effort, no matter how feeble, on the part of a respirator patient to breathe.

Many different schemes have been employed in attempts to solve the respirator problems presented. Most have either presented new problems or only partially solved the problems presented, or both. Most of these devices have thus met special needs as presented by specific problems and have, therefore, seved narrow purposes. These prior art devices, among other disadvantages, have been unreliable and unpredictable in operation under continued use and have been expensive and complicated to manufacture. Some of these prior art devices have been described in the following listed patents:

| Pat. No. | Title | Patentee |
| --- | --- | --- |
| 3,903,876 | Respiration Monitor | T. R. Harris |
| 3,645,133 | Electronic Spirometer | P. G. Simeth |
| 3,438,254 | Fluid Flow Detector | E. B. Seeley |
| 3,368,212 | Gas Flow Monitor | S. D. Klyce |
| 3,316,902 | Monitoring System for Respiratory Devices | H. T. Winchel |
| 3,085,431 | Flow Measuring Apparatus | A. J. Yerman |
| 3,972,327 | Respirator | H. Erust et al |
| 3,434,471 | Therapeutic Intermittent Positive Pressure Respirator | M. D. Liston |
| 3,220,255 | Thermal Mass Flowmeter | R. Scranton |

Upon examination of the above listed patents, the following analyses were made by Applicant and are submitted herewith for the convenience of the Examiner.

With respect to the Respiration Monitor, U.S. Pat. No. 3,903,876, to Harris, it is observed that this device would not be suited for use with a ventilator because it is not intended for use in closed system. The tubes are open to the atmosphere at several points including right at the patient, which construction will not operate satisfactorily with a positive pressure ventilator. The device has three additional disadvantages, among others, when compared with Applicants' invention. First, this device is designed to sense flow irrespective of direction. It is thus possible that an extra breath could be delivered when the patient needs to exhale rather than to inhale. Second, because all directional flow is sensed, there may be less dead time in which the thermistor can recover. And third, it is felt that is would be impossible to achieve the sensitivity that has been achieved with Applicants' invention.

With respect to the Electronic Spirometer, U.S. Pat. No. 3,645,133, to Simeth et al, it is observed that this device places a thermistor in line to measure patient flow with a second thermistor placed separately for temperature compensation. Since the thermistor is located in the main line, the cross-section at that point must be sized for full patient flow. The result is that a relatively large volume of air must move past the thermistor which means poor sensitivity and poor response time in comparison with Applicants' invention.

With respect to the Fluid Flow Detector, U.S. Pat. No. 3,438,254, to E. B. Seeley, it is noted that this device is also a main line sensing system subject to the disadvantages mentioned above. It also appears that this method is more complex and bulky than Applicants' invention.

With respect to the Gas Flow Monitor, U.S. Pat. No. 3,368,212, to S. D. Klyce, it is noted that a pressure differential between patient system and atmosphere caused by patient flow is relied on to cause airflow through a tube to cool a thermistor. Since the device described herein does not use a closed system, it would not be suitable for use with a positive pressure ventilator.

The greatest part of the patent to H. T. Winchel et al for a Monitoring System for Respiratory Devices, U.S. Pat. No. 3,316,902, deals with the circuitry and basic principles of breath rate monitors and patient assist function. The thermistor probe in this device is mounted directly to the body of the patient. There are several problems with this approach. Among them: (1) There is a shock hazard involved whenever an electrical device is mounted directly to a patient. If the thermistor were insulated sufficiently well to prevent all danger, the sensitivity or response time would be adversely affected. (2) At the patient, there is a great deal of humidity, mucus, and miscellaneous foreign matter which could accumulate on the thermistor and thus affect its performance. (3) Anything outside the ventilator which must be handled by therapists, nurses, and other personnel is subject to abuse and breakage. (4) If the thermistor is in contact with the patient, it needs to have provisions for disconnecting it from the ventilator to sterilize it. It must also be able to withstand sterilizing temperatures. It is felt that these disadvantages weigh very heavily against the device of this patent in respect of Applicant's invention.

Another interesting patent brought to Applicants' attention is the Flow Measuring Apparatus, U.S. Pat. No. 3,085,431 to A. J. Yerman et al. One major disadvantage of the device described is its complexity. It is designed for accurate measurement rather than merely to sense an attempted initiation of flow.

It would thus be a great advantage to the art to provide a system of greater sensitivity to patient effort than that presently available.

SUMMARY OF THE INVENTION

In view of the above stated problems associated with the prior art, an object of the present invention is the provision of a more sensitive means of sensing patient breathing effort than is presently available.

Another object of the present invention is the provision of the above more sensitive means in a form such as may be utilized to modify existing systems.

A further object of the present invention is the provision of the above means in an economical and convenient package so as to modify existing systems.

A still further object of the present invention is the provision of a device capable of differentiating between an inhalation effort and an exhalation effort.

The device of the invention provides a sensing mechanism that utilizes a thermistor assembly associated with a sensitive diaphragm, a chamber and a small diameter tube arranged to cause a large velocity of fluid flow past the thermistor assembly to provide maximum directional sensitivity to a patient's effort to breathe as hereinafter described.

BRIEF DESCRIPTION OF THE DRAWINGS

Further advantages and features of the present invention will be more fully apparent to those skilled in the art to which the invention pertains from the ensuing detailed description thereof, regarded in conjunction with the accompanying drawings, wherein like reference characters refer to like parts throughout and in which.

DETAILED DESCRIPTION

Although specific embodiment of the invention will now be described with reference to the drawings, it should be understood that such embodiments are by way of example only and merely illustrative of but a small number of the many possible specific embodiments which can represent applications of the principles of the invention. Various changes and modifications obvious to one skilled in the art to which the invention pertains are deemed to be within the spirit, scope and contemplation of the invention as further defined in the appended claims.

Figure 1:
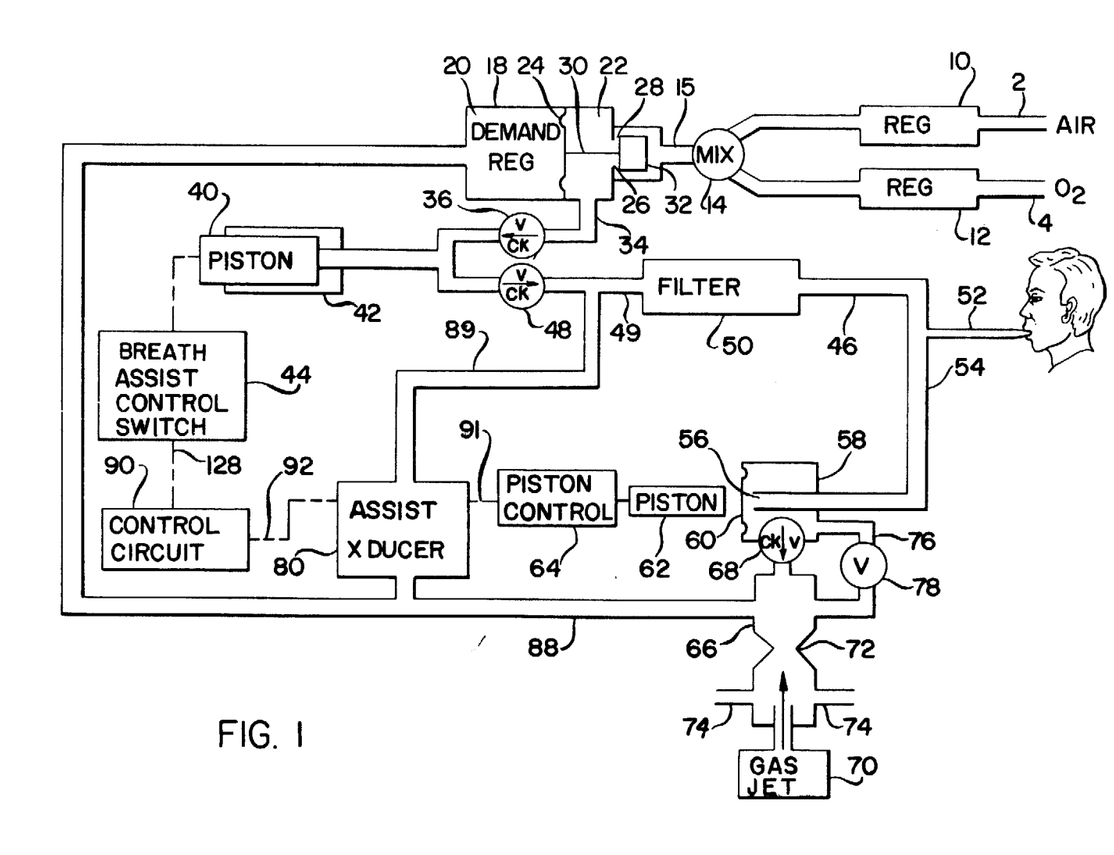
FIG. 1 is an idealized conceptual block flow diagram illustrating the general characteristics of a modern ventilator.

Referring to FIG. 1 with greater particularity, a generalized flow diagram illustrating the characteristics of a modern ventilator is presented. Air is received in an air inlet 2 and fed through regulator 10 into mixing valve 14. Oxygen, likewise, is received in an oxygen inlet 4 and fed through oxygen regulator 12 to the same mixing valve 14. After being mixed in mixing valve 14, the air/oxygen mixture is received in inlet chamber 15 of a demand regulator 18 which is further divided into a reference chamber 20 and a sensing chamber 22, the last two chambers being separated by a flexible, resilient diaphragm 24. Inlet chamber 15 and sensing chamber 22 are separated by a wall 26 having a central opening 28 through which a rod 30 extends from the diaphragm 24 to the interior of chamber 15. A stopper 32, affixed to the end of rod 30 within chamber 15, normally abuts the dividing wall 26 to cover opening 28, thereby preventing any flow of air between chambers 15 and 22. This flow restriction is removed when the gas pressure in chamber 22 is reduced by a predetermined amount while the gas pressure in chamber 20 remains at a constant level. In this event, diaphragm 24 flexes into the area formally occupied by chamber 22 (to the right in FIG. 1), moving stopper 32 out of contact with the dividing wall 26 and allowing the gas mixture to flow from air and oxygen supplies into air and oxygen inlets 2 and 4, respectively, through regulators 10 and 12, into and through mixing valve 14 and chamber 15 into chamber 22. The demand regulator 18 thus functions much as a scuba tank regulator in which a pressure drop is produced when the user attempts to inhale, opening up a line from an air supply.

Sensing chamber 22 is connected via a conduit 34 and check valve 36 to a breath assist mechanism which includes a piston 40 slidably lodged within a cylinder 42. A breath assist control switch 44 governs the operation of the breath assist mechanism. A negative pressure is created in sensing chamber 22 when piston 40 is drawn backward (to the left in FIG. 1), thus flexing the diaphragm 24 and thereby uncovering opening 28 to enable an airflow from air and oxygen supplies through regulators 10 and 12, into and through mixing valve 14, through chamber 22, conduit 34 and check valve 36 into cylinder 42 as long as piston 40 continues to move backward. Breath assist control switch 44 actuates the breath assist mechanism when commanded by signalling piston 40 to drive forward, thus charging the air mixture in cylinder 42 into the patient supply conduit 46 by way of check valve 48 and filter 50. The volume of gas delivered to the patient may be either a preset amount, or determined dynamically by providing well-known apparatus to measure the patient's lung pressure and terminate forward movement of piston 40 when lung pressure reaches a desired level.

A patient supply conduit 46 provides a gas conduit between the breath assist apparatus and the patient. The conduit system includes a check valve 48 which prevents a backflow of exhaled gas from the patient to the breathing air sources, and a filter and/or humidifying device 50 to treat the breathing air before delivery to the patient. An endotracheal tube 52 may be fitted to the conduit system in a tee connection to conduct air to and from the patient.

The conduit system further includes an outlet or expiratory branch 54 having an outlet port 56 enclosed within a variable pressure chamber 58, one wall of which forms a diaphragm 60 in registry with outlet port 56. A piston 62 is located to alternately flex the diaphragm 60 to a position blocking the outlet port 56 when the piston is in a forward position, and to release the diaphragm 60 and allow gas to flow out of the conduit system 54 through outlet port 56 when the piston 62 is in a retracted position. A piston control device 64 such as a solenoid under the control of an assist transducer 80 and control circuit 90 causes the piston 62 to block the outlet port 56 during inspiration and uncover the port during expiration.

While the patient's breathing behavior may be sensed in a number of ways, such as by measuring the pressure within the conduit system 46 and actuating the breath assist mechanism whenever the pressure falls below a particular level, the present invention contemplates a unique and ultrasensitive method to be explained subsequently.

In the conventional ventilator, chamber 58 communicates with a second chamber 66 through a check valve 68 that permits a gas flow only from chamber 58 into chamber 66. The pressure within chamber 66 is positively maintained at a constant level by means of a gas jet source 70 that delivers a steady jet stream through a venturi 72 and into the chamber 66. A number of outlet orifices 74 are located between gas jet source 70 and venturi 72 to allow gas exhaled by the patient to exit from the respirator system. Gas jet source 70 is adjustable within a range that permits the pressure inside chamber 66 to be set between zero and 15 centimeters of water gage (zero to approximately 0.2 pounds per square inch gage). A bleeder conduit 76 enables a backflow of gas from chamber 66 to enter chamber 58, with an adjustable needle valve 78 forming a restriction in the line to limit the flow rate (gas flowing in the opposite direction, from chamber 58 to chamber 66, is transmitted through check valve 68). Needle valve 78 may be adjusted from a full open position, at which the gas flow through the bleeder conduit 76 is substantially unrestricted, to a completely closed position.

Dynamic control of the breath assist mechanism starts at assist transducer 80. A pressure differential between PEEP reference conduit 88 and connecting tube 89 must be sensed therein. The acronym PEEP denotes positive expiratory end pressure. PEEP pressure is incident also at PEEP reference chamber 20. Assist transducer 80 develops signal information useful to control piston control device 64 by way of signal line 91 and breath assist control circuit 90 by way of signal line 92. Breath assist control switch 44 is responsive to signal transmitted by way of signal line 128 from control circuit 90 and thereby controls piston movement in piston cylinder 42. As is evident from the foregoing discussion, the sensitivity of the total ventilator system is dependent upon the sensitivity of assist transducer 80. Therefore, in order to develop a more sensitive system, one of the most important elements is the sensitivity of assist transducer 80. It is to this component in the overall ventilator system that Applicant's invention is primarily directed.

Figure 2:
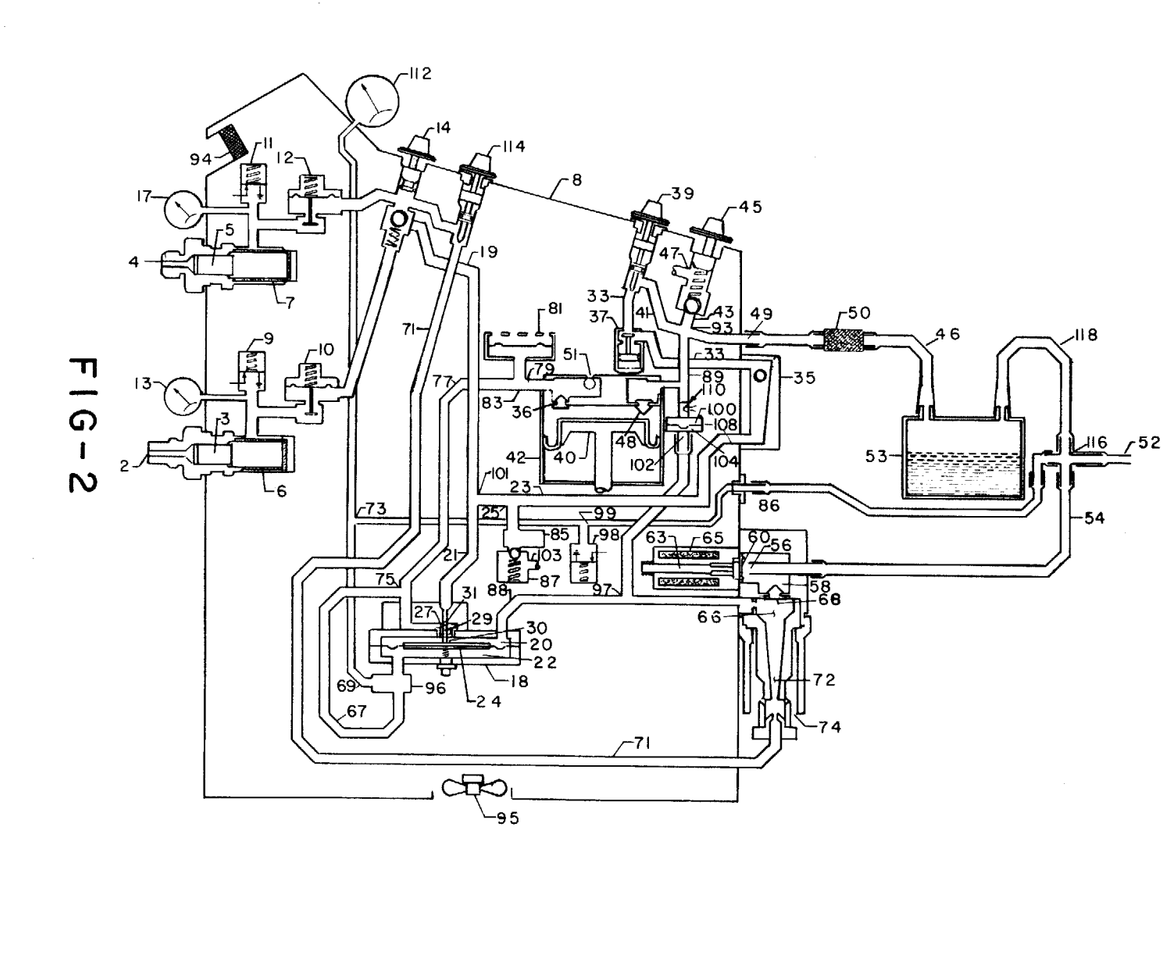
FIG. 2 is a combined perspective and flow schematic of a ventilator showing incorporation of Applicants' inventive device therein.

In FIG. 2, there is illustrated a system in which the sensing transducer as contemplated by Applicant's invention has been incorporated. As in FIG. 1, air and oxygen inlets are denoted respectively by numerals 2 and 4. The air accepted by the system and incident at mixing valve 14 has been processed through air check valve 3, air filter 6, air pressure alarm switch 9 and air regulator 10. An air inlet pressure gage 13 monitors the incident air pressure. In like manner, the oxygen incident at mixing valve 14, after having been accepted by the machine through oxygen inlet 4 and led through oxygen check valve 5 and oxygen filter 7 is incident upon oxygen pressure alarm switch 11 and regulated by oxygen regulator 12. Again, an oxygen inlet pressure gage is denoted by the numeral 17. When the apparatus is mounted in a cabinet as indicated in this FIG. 2, it is necessary to have cooling air. Therefore, a cooling air intake is identified by the numeral 94 while the cooling air exhaust fan is identified by the numeral 95. The control console and cabinet have been assigned the identifying numeral 8. The PEEP reference pressure system comprises the constant pressure chamber 66, PEEP venturi 72 and outlet orifices 74 with a gas jet supply conduit 71. This pressure is incident at PEEP control valve 114. The breathing gas as blended in mixing valve 14 is fed through a conduit 19 by way of a tee 101 into conduits 23 and through flowmeter 35 through safety valve 37 and conduit 33 to flow control valve 39. Flow control valve 39 supplies the blended gas by way of conduit 41 through cross coupling 93 into filter 50 thence through patient supply conduit 46 to a humidifier 53. After being humidified, the breathing gas is then supplied through conduit 118 to cross connector 116 and finally to endotracheal tube 52 to the patient. As may be easily seen, there are many auxiliary circuits and safety devices included. For example, a part of the piston system, comprising the piston 40 and piston cylinder 42, has to do with a safety valve 50 and a compliance chamber 81. Upon rapid retraction of piston 42, compliance chamber 81 prevents outside air from contaminating the system. As is seen, compliance chamber 81 is in fluid communication with piston cylinder 42 by means of a tee 79 and a conduit 83. A check valve 36 allows breathing gas to be charged into cylinder 42. Another check valve 48 allows breathing gas to be supplied from cylinder 42 into the patient supply conduit.

It is interesting to trace another fluid path followed by the air/oxygen mixture. A tee 25 permits the pressure of the air/oxygen mixture in conduit 19 to influence a bleed solenoid 85 that controls a vent 103 by means of bleed valve 87. This bleed system is instrumental in maintaining desired gas mixtures under certain minimum flow conditions, however, when the system is not in use, the bleed valve should be closed in order to conserve gas. The bleed solenoid 85 performs the function of shutoff for the valve 87.

Tee 101 supplies the air/oxygen mixture to demand regulator 18. Demand regulator 18 comprises an opening 27 directly in fluid communication with conduit 19 by means of tee 101 and conduit 21; a ball seal 31; a valve seat 29; a rod 30 attached to a diaphragm 24; and PEEP and reference sensing chambers 20 and 22, respectively. The operation of demand regulator 18 is effected by means of the interrelationships between demand solenoid 96 and its interconnections by means of conduits 67, 69 and tees 73 and 75. Such connections and relationships are common in the art and are important in the instant case only insofar as an overall system is rendered more understandable by such exposition.

Expiratory conduit 54, as explained with reference to FIG. 1, connects to variable pressure chamber 58 which contains outlet port 56 which is in turn controlled by diaphragm 60 under the action of armature 63 which is activated by exhalation solenoid 65. The constant pressure reference chamber, as noted above, is identified by the numeral 66, while the expiratory check valve permitting only one way fluid communication from variable pressure chamber 58 to constant pressure reference chamber 66 is denoted by the numeral 68.

The constant reference pressure developed in chamber 66 is the PEEp reference pressure for the system as set and controlled by PEEP control valve 114 and this reference pressure is incident in the PEEP reference chamber of demand regulator 18 by means of conduit 88. A tee connection 97 in conduit 88 furnishes PEEP reference pressure to thermistor sensing probe assembly 100. Thermistor sensing probe assembly 100 comprises a reference tube 102 for receiving PEEP reference pressure; a chamber 104; a diaphragm 108 isolating chamber 104 from PEEP reference pressure; a sensing tube 106 (FIG. 3) and a thermistor assembly. This total assembly is connected by means of a tee to the piston cylinder 42 and by means of conduit 89 to the patient supply conduit 49. A pressure relief valve 45 is connected by means of a tee 43 into cross coupling 93 and permits venting of any excess pressure developed in this conduit line to atmosphere by way of vent 47.

An additional auxiliary fluid circuit is provided by the proximal airway conduit 86 connected to cross connector 116. Proximal airway conduit 86 is connected to pressure transducer 98 by a tee 99 and to proximal airway pressure gage 112 and demand solenoid 96 by means of tee 73.

The operation of compliance chamber 81 ensures that the breathing gas supplied to the patient does not become contaminated by way of safety valve 51. For example, under the condition that piston 40 begins to retract rapidly, a negative pressure, great enough to open safety valve 51 may be developed. In that event, room air could be sucked in through check valve 36 and upset the air/oxygen balance intended to be furnished to the patient as charged into cylinder 42. However, since the compliance chamber 81 is in the system, its diaphragm will deflect and allow gas to flow from the capacity of the compliance chamber itself very easily into the piston cylinder 42, thus allowing demand valve 18 time in which to open completely and thus furnish the desired air/oxygen mixture through conduit 77 into the cylinder 42. It is easily determined that the overall system here presented can be no more sensitive that the thermistor sensing probe assembly 100 which senses a feeble effort to breathe by a patient, as will be explained with reference to FIGS. 3, 4 and 5.

Figure 3:
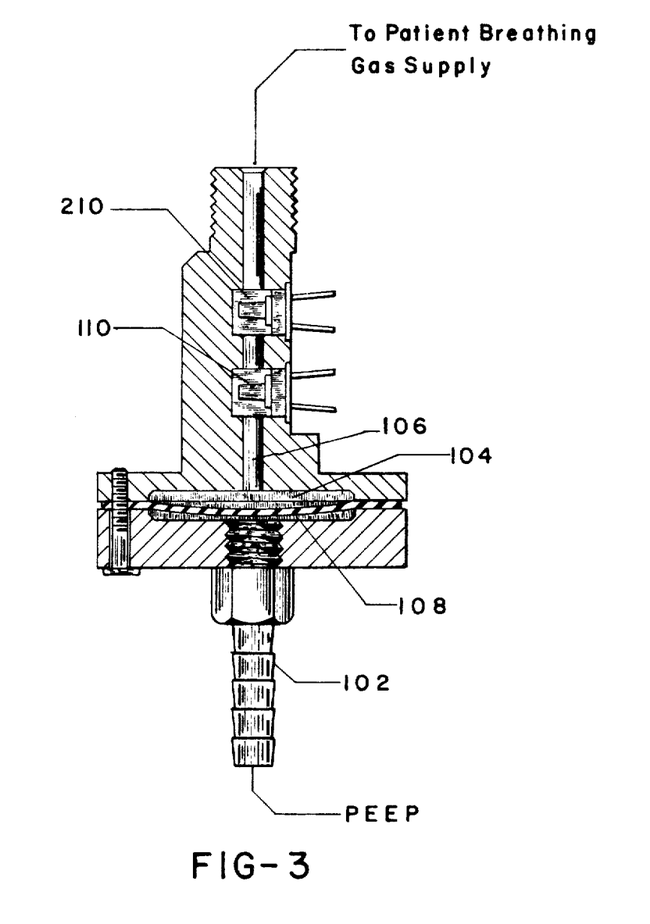
FIG. 3 is a detailed perspective in cross-section of one configuration of the thermistor sensing probe assembly of the invention.

Referring now more particularly to FIG. 3, one configuration of the thermistor sensing probe assembly is shown in detailed cross-section. At the bottom of the figure, reference tube 102 transmits the influence of PEEP reference pressure to diaphragm 108 situated in chamber 104. Sensing tube 106 contains self-heated thermistors 110 and 210 between chamber 104 and conduit 89 that supplies the patient breathing gas. With reference once more to FIG. 2, it may be seen that a patient attempt to breathe incident an endotracheal tube 52 will be transmitted through conduit 118 through patient supply conduit 46, filter 50, and be experienced through conduit 89 by the thermistor sensing probe assembly 100. With reference now back to FIG. 3, a negative pressure applied through sensing tube 106 will allow diaphragm 108 to deflect rapidly upward to the limits of its travel in chamber 104 thus causing the volume of gas in that chamber to move very rapidly through sensing tube 106 and past thermistors 110 and 210, thus causing very rapid cooling of thermistor 110 and subsequent alteration of its resistance so as to derive an electrical signal. Both thermistors are heated by a constant current source, such as that indicated by the numeral 150 in FIG. 7. Therefore, in the situation just described, heated air from thermistor 110 passes over thermistor 210 thus preventing thermistor 210 from being cooled by the flow of air, therefore, thermistor 210 does not experience as sudden a change in its resistance as that experienced by thermistor 110. The above description assumes an attempt on the part of the patient to inhale.

In the event of a patient attempt to exhale, the reverse effect obtains. That is, a positive pressure applied through conduit 89 will be experienced in sensing tube 106 until the limit of capacity of chamber 104 has been reached. The air then moving past thermistor 110 will be preheated by thermistor 210 so that thermistor 110 does not cool significantly. Thus, thermistor 110 will not experience as sudden a change in its resistance as that experienced by thermistor 210. The device just described, therefore, contemplates means for developing different signals, one as a function of a patient's attempt to inhale, and the other as a function of a patient's attempt to exhale. It has been determined that through the utilization of very flexible diaphragm materials and a very small cross-section sensing tube, that small volume of air making up the capacity of chamber 104 can be caused to move past the thermistor assembly at a very rapid rate, thus causing very rapid cooling and a subsequent rapid change in the resistance of a selected thermistor as detailed above in accordance with inhalation or exhalation attempts.

Figure 4:
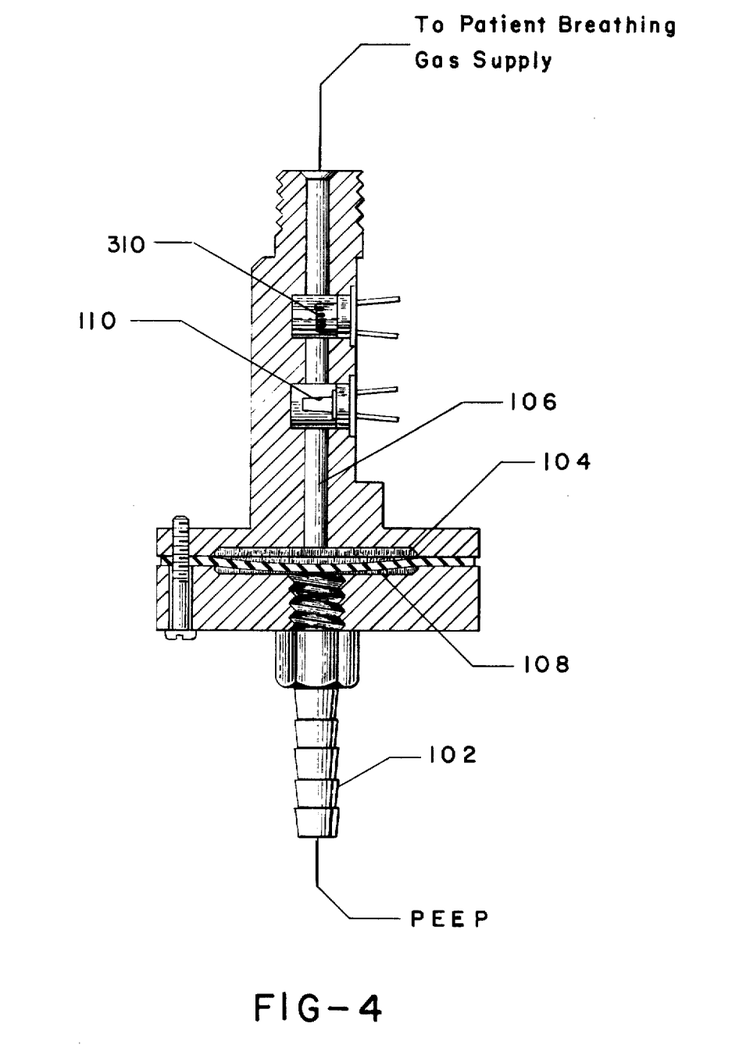
FIG. 4 is a detailed perspective in cross-section of another configuration of the thermistor sensing probe assembly of the invention.

Reference now to FIG. 4 will permit analysis of another embodiment of the present invention. The figure illustrates the sensing probe assembly in detailed cross-section. At the bottom of the figure, reference tube 102 transmits the influence of PEEP reference pressure to diaphragm 108 situated in chamber 104. Sensing tube 106 in the instant configuraton contains thermistor 110 and heater 310 between chamber 104 and conduit 89 that supplies the patient breathing gas. Again, with reference to FIG. 2, it may be seen that a patient's attempt to breathe incident an endotracheal tube 52 will be transmitted through conduit 118, through patient supply conduit 46, filter 50, and be experienced through conduit 89 by the thermistor sensing probe assembly 100. With reference now back to FIG. 4, a negative pressure applied through sensing tube 106 will allow diaphragm 108 to deflect rapidly upward to the limits of its travel in chamber 104, thus causing the volume of gas in that chamber to move very rapidly through sensing tube 106 and past thermistor 110 and heater 310, thus causing very rapid cooling of thermistor 110 and subsequent alteration of its resistance so as to derive an electrical signal.

In the event of a patient attempt to exhale, a different effect obtains. That is, a positive pressure applied through conduit 89 will be experienced in sensing tube 106 until the limit of capacity of chamber 104 has been reached. The air moving past thermistor 110 will be preheated by heater 310 so that the temperature of the thermistor 110 will rise. Thus, thermistor 110 will experience change in its resistance in the opposite sense from that resulting from the flow of air in the direction described with respect to patient's inhalation. The device thus described, therefore, again contemplates means for developing different signals, one as a function of a patient's attempt to inhale, and the other as a function of a patient's attempt to exhale. Thus, air flowing out of the chamber 104 and through the sensing tube 106 past thermistor 110 will cause rapid cooling of that thermistor and a subsequent sudden change in its resistance, while air flowing in the opposite direction, that is, into chamber 104, will be preheated by heater 310 before its incidence upon thermistor 110, thereby causing an opposite change in the resistance of thermistor 110.

Figure 5:
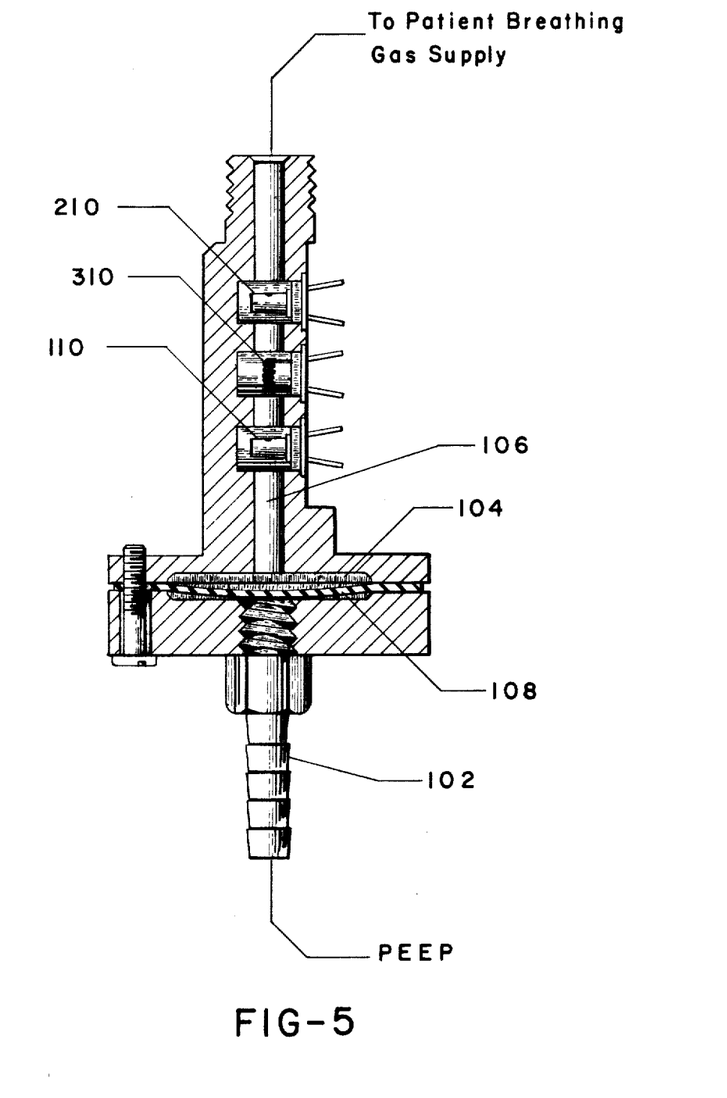
FIG. 5 is a detailed perspective in cross-section of yet another configuration of the thermistor sensing probe assembly of the invention.

Reference now to FIG. 5 will permit analysis of still another embodiment of the present invention. The figure illustrates the sensing probe assembly in detailed cross-section. At the bottom of the figure, reference tube 102 transmits the influence of PEEP reference pressure to diaphragm 108 situated in chamber 104 as in the two previous configurations. Sensing tube 106 in the instant configuration contains thermistor 110, heater 310, and thermistor 210 between chamber 104 and conduit 89 that supplies the patient breathing gas. Again, with reference to FIG. 2, it may be seen that a patient's attempt to breathe incident an endotracheal tube 52 will be transmitted through conduit 118, through patient supply conduit 46, filter 50, and be experienced through conduit 89 by the thermistor sensing probe assembly 100. With reference now back to FIG. 5, a negative pressure applied through sensing tube 106 will allow diaphragm 108 to deflect rapidly upward to the limits of its travel in chamber 104, thus causing the volume of gas in that chamber to move very rapidly through sensing tube 106 and past thermistor 110, heater 310, and thermistor 210, thus causing very rapid cooling of thermistor 110 along with a lesser cooling of thermistor 210, since the air passing thermistor 210 will have been subject to the heating influence of heater 310. The subsequent alteration of the resistance of thermistor 110 will thus be greater than the alteration of the resistance of thermistor 210, thus electrical signals of different magnitudes may be derived. Heated air from thermistor 110 will pass the heater 310 and be further heated before its contact with thermistor 210, thus thermistor 210 will be very slightly cooled, if at all, by the flow of air. Therefore, thermistor 210 will not experience as sudden a change in its resistance as that experienced by thermistor 110. It will be noted that the above description assumes an attempt on the part of the patient to inhale.

In the event of a patient's attempt to exhale, a different effect obtains. That is, a positive pressure applied through conduit 89 will be experienced in sensing tube 106 until the limit of capacity of chamber 104 has been reached. The air then moving past thermistor 210 will be preheated by heater 310 before its incidence upon thermistor 110. Thus, thermistor 110 will not cool significantly and therefore will not experience as sudden a change in its resistance as that experienced by thermistor 210, subject to the unheated incident air. The configuration thus described, therefore, also contemplates means for developing different signals, one as a function of a patient's attempt to inhale, and the other as a function of a patient's attempt to exhale.

With reference to FIG. 1, it may be seen that these heretofore described sudden changes in electrical properties may be used in the assist transducer so to effect the operation of control circuit 90 and piston control device 64. It has been determined that thermistor sensing probes in the manner contemplated by the invention have had sensitivities of orders of magnitude greater than prior art sensing devices.

FIGS. 7 through 10 illustrate exemplary discriminating circuits for distinguishing an inhalation-induced signal from an exhalation-induced signal, so that an appropriate response can be induced in the assist cycle controlling logic circuit of FIG. 6, which will be described later on.

Figure 7:
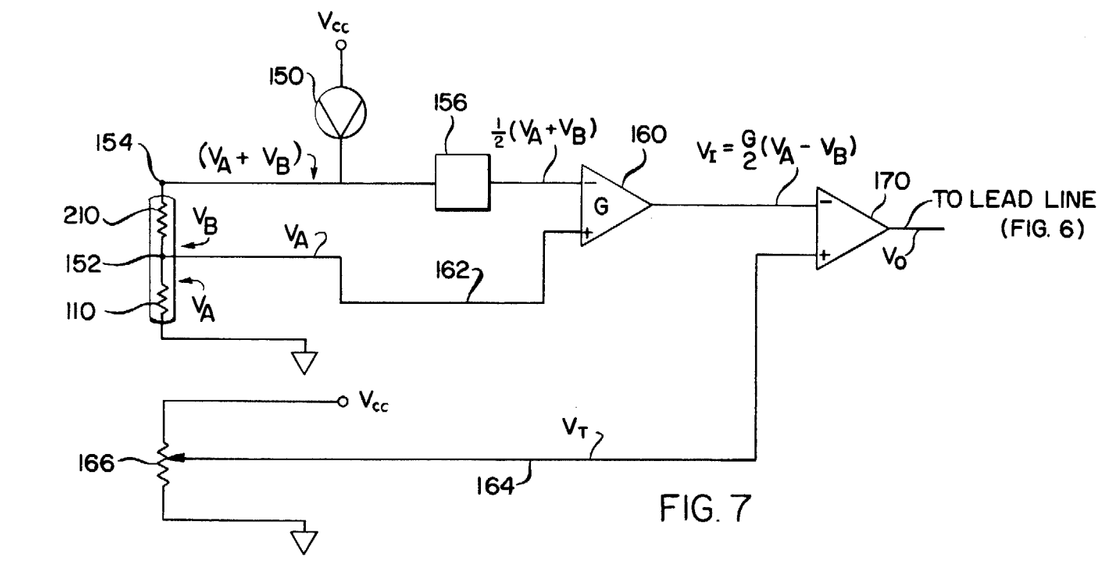
FIG. 7 is a schematic diagram of one electronic circuit utilized in connection with the logic circuit of FIG. 6.
Figure 8:
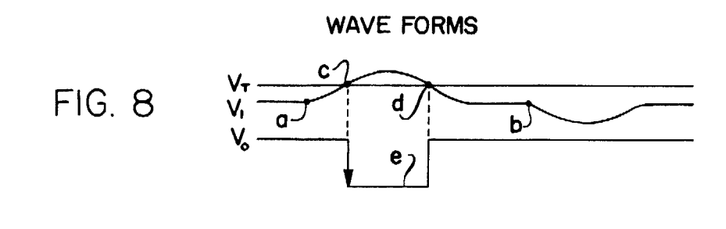
FIG. 8 is a graphic representation of signal waveforms associated with the circuit of FIG. 7.

FIG. 7 illustrates such a discriminating circuit for use with the thermistor assemblies of FIGS. 3 and 5. It can be seen that the relative cooling of the thermistors 110 and 210 is reflected in voltage drops $V_A$ and $V_B$, respectively, across the thermistors 110 and 210, when current from a constant current generator 150 is driven through the two thermistors wired in series, as shown. The thermistors 110 and 210 are connected at a junction 152, which presents a voltage $V_A$ equal to the voltage drop across the thermistor 110, while a point 154 on the opposite side of the thermistor 210 from the junction 152 presents a voltage $V_A + V_B$, equal to the total voltage drop across the two thermistors.

The voltage $V_A + V_B$ is attenuated to $\frac{1}{2}(V_A + V_B)$ by an attenuator 156, and this signal is then inputted to a differential amplifier 160. The other input to the amplifier 160 is a line 162 carrying the voltage $V_A$. The amplifier 160 has a gain G, so that the amplifier output signal has a voltage $V_I = G/2 (V_A - V_B)$. This voltage $V_I$, being proportional to the difference in the respective voltage drops across the two thermistors 110 and 210, will increase from a base value as the thermistor 110 cools relative to the thermistor 210, and decreases from the base value as the thermistor 210 cools relative to the thermistor 110. Thus, $V_I$ will increase during a patient attempt to inhale, and decrease during a patient attempt to exhale. This is shown graphically in FIG. 8, where the point "a" on the waveform marked $V_I$ represents the onset of an inhalation attempt, and the point "b" represents the onset of an exhalation attempt.

A threshold voltage $V_T$ is generated on a line 164, with its value adjusted by means such as a potentiometer 166. This voltage $V_T$, along with the voltage $V_I$ (from the output of the differential amplifier 160) is fed into a comparator 170. The result, as illustrated graphically in FIG. 8, will be a negative transition in the output voltage $V_O$ of the comparator 170 when $V_I$ rises to the value of $V_T$, corresponding to the cooling of the thermistor 110 by a predetermined amount relative to the thermistor 210, which, in turn, corresponds to a predetermined inhalation effort. This "triggering value" of $V_I$ is illustrated by the point "c" in FIG. 8. When $V_I$ then decreases to the level of $V_T$ (at the point "d" in FIG. 8), the result is a positive transition in the comparator output voltage $V_O$, thereby resetting $V_O$ to its "high" level, where it will remain throughout the exhalation part of the respiratory cycle, beginning at point "b".

As will be made clear later on, the "low" or negative region of $V_O$ (labeled "e" in FIG. 8) corresponds to an enabling signal on an input lead 107 of the assist cycle actuator circuit illustrated in FIG. 6. Thus, the assist cycle will be initiated when a predetermined inhalation effort is sensed. On the other hand, when $V_O$ is at its "high" level, the signal on lead 107 will be in the nature of a blocking signal. Thus, since the level of $V_O$ will be "high" when exhalation is sensed by the cooling of the thermistor 210 relative to the thermistor 110, the assist cycle cannot be mistakenly actuated in response to an exhalation effort, rather than an inhalation effort.

It should be noted that the level of $V_T$ should be suitably selected, at a value slightly above the base level of $V_I$, by means of the potentiometer 166, to preclude accidental triggering of the assist cycle due to inherent or induced electrical "noise" in the circuitry, and to compensate for the tolerances in the electrical characteristics of the electrical components of the circuitry, particularly the thermistors 110 and 210.

Figures 9, 10:
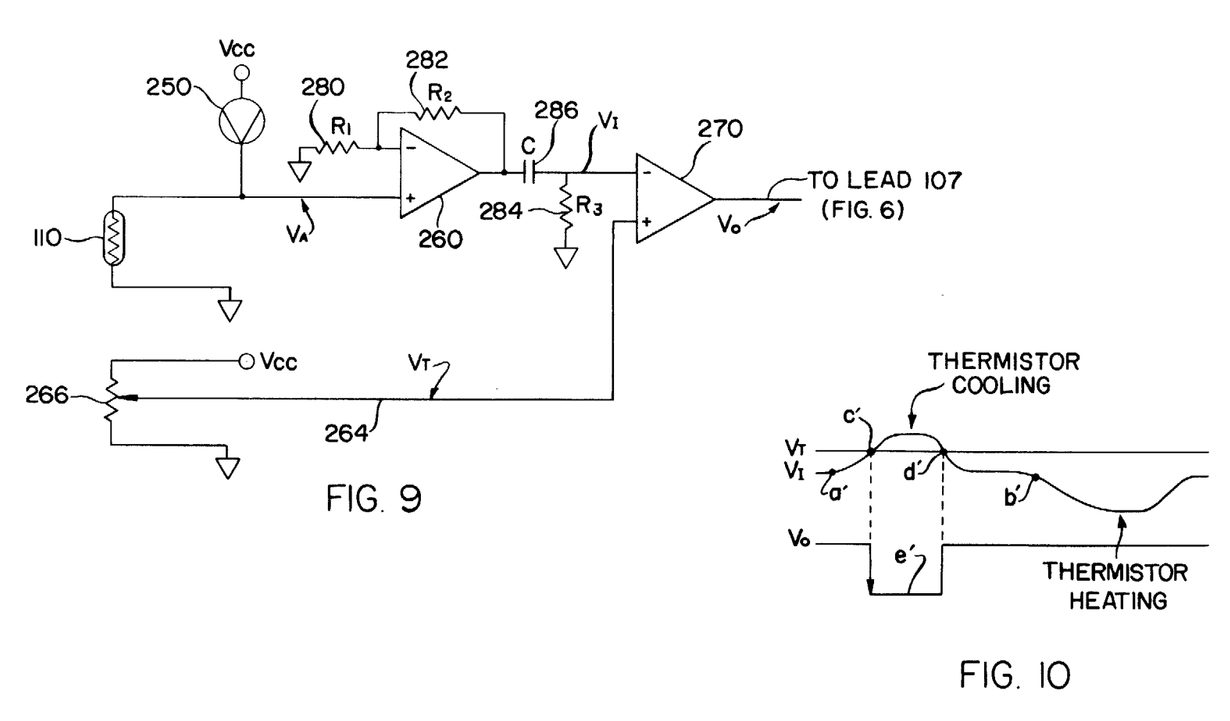
FIG. 9 is a schematic diagram of a second electronic circuit utilized in connection with the logic circuit of FIG. 6.
FIG. 10 is a graphic representation of signal waveforms associated with the circuit of FIG. 9.

FIG. 9 illustrates a discriminating circuit for use with the thermistor assembly of FIG. 4, which uses one thermistor 110 and a separate heating element 310 (which can be, if desired, a second thermistor driven by a constant current so that it functions solely as a heating element).

A temperature change sensed by the thermistor 110 is reflected in a change in the voltage across the thermistor, when current from a constant current generator 250 is driven through the thermistor. This thermistor output signal, having a voltage $V_A$, is fed into an operational amplifier 260, which is biased by a pair of resistors 280 and 282, having resistances $R_1$ and $R_2$, respectively. The amplifier 260 thus has a gain $G = (1 + R_2/R_1)$, so that the amplifier output signal has a voltage of $V_A(1 + R_2/R_1)$. The amplifier output signal is fed into a filter comprising a capacitor 286, having a capacitance C, and a resistor 284, having a resistance $R_3$. The capacitance C and resistance $R_3$ are selected to provide a time constant $R_3C$ which removes any DC component of the thermistor output signal, leaving an intermediate voltage $V_I$ for input to a comparator 270.

The voltage $V_I$, as shown graphically in FIG. 10, is proportional to changes in the thermistor voltage $V_A$ resulting from temperature changes experienced by the thermistor 110. Thus, as the thermistor 110 is cooled by an inhalation-induced air flow through the sensing tube 106, the voltage $V_A$ increases, and the voltage $V_I$ will increase proportionately from a base level, beginning at the point a' in FIG. 10, which represents the initiation of an inhalation effort. Likewise, when the temperature of the thermistor 110 is caused to increase by an exhalation-induced air flow through the tube 106, the voltage $V_I$ decreases from the base level in proportion to the resulting decrease in $V_A$, beginning at the point b' which represents the onset of an exhalation effort.

As in the previously described circuit of FIG. 7, a threshold voltage $V_T$ is generated on a line 264, and adjusted by a potentiometer 266. The threshold voltage $V_T$ is inputted, along with the voltage $V_I$, to the comparator 270. (The gain G of the amplifier 260 should be selected to provide sufficient amplification of the thermistor signal so that the voltage $V_I$ is of a compatible magnitude with that of the threshold voltage $V_T$ and with the operational characteristics of the comparator 270).

The result is illustrated graphically in FIG. 10. The comparator output voltage $V_O$ undergoes a negative transition to its "low" value e' when $V_I$ rises to the value of $V_T$, corresponding to the cooling of the thermistor 110 by a predetermined amount in response to a predetermined inhalation effort. This triggering value of $V_I$ is illustrated by the point c' in FIG. 10. When $V_I$ then decreases to the level of $V_T$ (at the point d' in FIG. 10), the result is a positive transition in the comparator output voltage $V_O$ to its "high" value, where it will remain throughout the exhalation part of the respiratory cycle.

Figure 6:
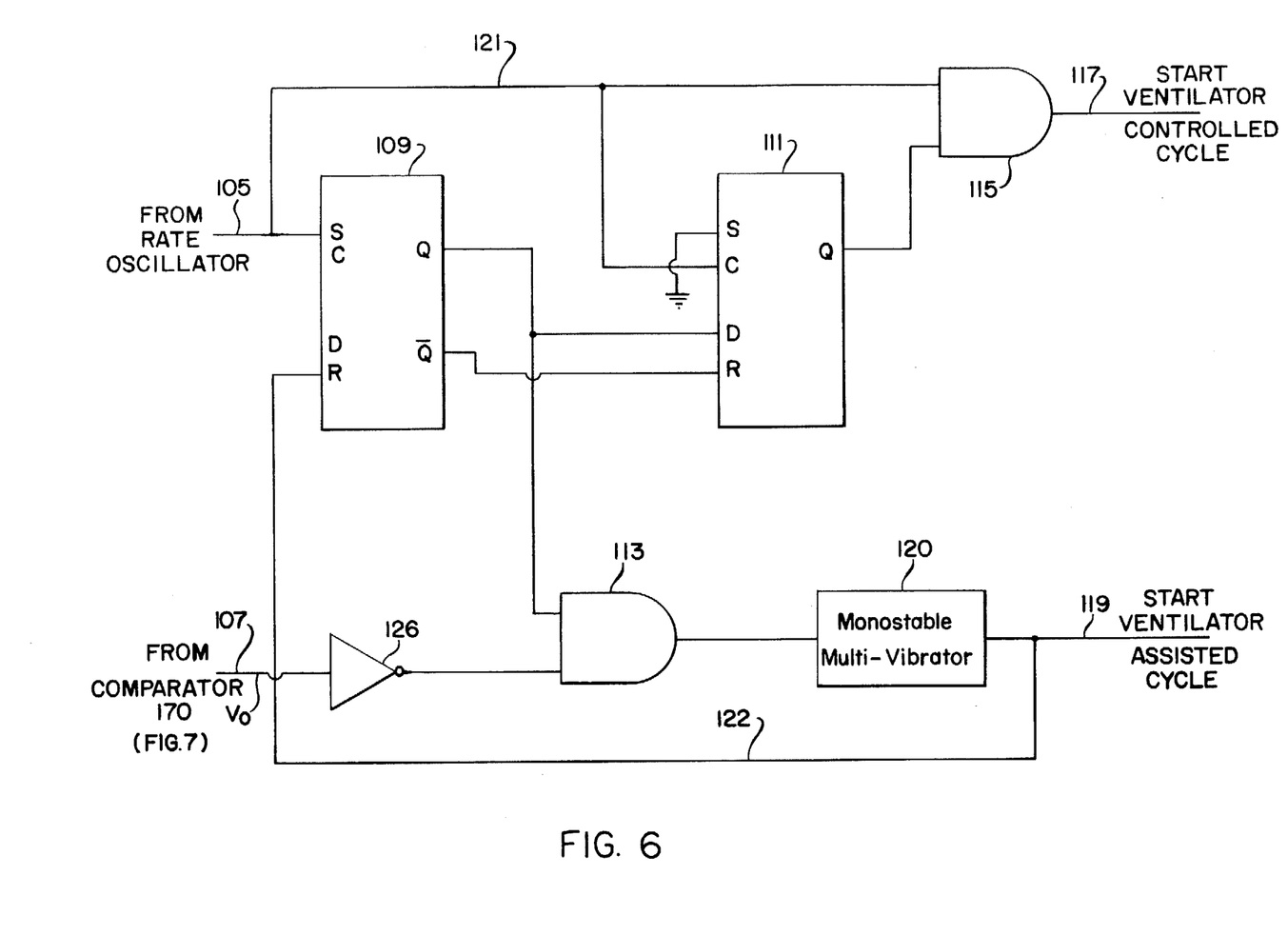
FIG. 6 is a logic diagram of a logic circuit such as might be utilized with Applicant's invention.

As will be presently explained, the low region e' corresponds to an enabling signal on input lead 107 of the assist cycle actuator circuit illustrated in FIG. 6. Thus, the assist cycle will be initiated when a predetermined inhalation effort is sensed. When $V_O$ is at its high value, however, a blocking signal will be imposed on the lead 107. Thus, since the value of $V_O$ is high when exhalation is sensed by a rise in temperature of the thermistor 110, the assist cycle cannot be mistakenly actuated in response to an exhalation effort.

FIG. 6 is illustrative of a logic circuit in which the comparator output signal $V_O$ might be employed. As is commonly known in the art, a rate oscillator (not shown) may be set to give an output pulse train at a desired breathing rate on a lead 105. The first such rate pulse received from the rate oscillator sets a first flip-flop 109, making its Q output high, thus enabling a first AND gate 113. Upon receipt of a negative value of the comparator output signal $V_O$ from the comparator 170 on line 107, an inverter 126 may operate "on" and amplify that pulse, which is transmitted to enabled AND gate 113, thereby supplying an input signal to monostable multivibrator 120. The resultant signal from monostable multivibrator 120 would be supplied to system command lead 119 commanding the ventilator to start an assisted cycle. At the same time, the signal from the multivibrator 120 is transmitted by a reset lead 122 to the reset terminal of the first flip-flop 109, thus disabling first AND gate 113 until a subsequent pulse is received on lead 105 from the system rate oscillator. It will be noted that the signal from the system rate oscillator is also incident upon a second flip-flop 111 of the D type (D for data) on a lead 121 and also this signal pulse enables a second AND gate 115. Whenever a signal is transmitted by way of this second flip-flop 111 so as to render its Q output high, a ventilator controlled cycle is started in response to an apneic condition of the patient.

It will be seen that when the pulse on lead 107 is positive, corresponding to a "high" value of $V_O$, the output from the inverter 126 will be "low", so that the AND gate 113 does not transmit. Thus, the assist cycle cannot be initiated in response to an exhalation effort, since an exhalation effort produces the "blocking" positive pulse on the lead 107, as previously discussed.

Thus there has been described a directional thermistor assist sensing device for assist-mode respirators, that will provide much greater sensitivity than has been known by the prior art. It has been demonstrated that the reliability, maintainability, and ease of operation have been highly enhanced through the novel advantages of the invention.

It is here pointed out that although the present invention has been shown and described with reference to particular embodiment, nevertheless various changes and modifications obvious to one skilled in the art to which the invention pertains are deemed to lie within the purview of the invention.

What is claimed and desired to be secured by Letters Patent of the United States is:

1. In a respiratory ventilator of the type having means for providing a respiratory assist cycle for a patient, a mechanism for controlling said assist cycle providing means, comprising:
    breathing conduit means adapted for fluid communication with the breathing passages of said patient;
    a sensing tube in fluid communication with said breathing conduit means and receptive to patient-induced respiratory pressures therein, said sensing tube having a restricted-diameter passageway therethrough which is subject to said patient-induced respiratory pressures;
    pressure-sensitive means coupled to said sensing tube and in fluid communication with said passageway, for generating a high velocity, low volume flow of gas through said passageway in a first direction in response to an inhalation-induced pressure sensed through said sensing tube, and in a second direction in response to an exhalation-induced pressure sensed through said sensing tube, the velocity and volume of said flow of gas being determined, at least substantially in part, by the restricted diameter of said passageway;
    fluid flow sensing means in said passageway for producing a first electrical output signal having a first predetermined output level in response to a flow of gas in said first direction and a second electrical output signal having a second predetermined output level different from said first predetermined output level in response to a flow of gas in said second direction; and
    control means, responsive to said first and second electrical output signals, for actuating said assist cycle providing means in response to said first electrical output signal, and blocking the actuation of said assist cycle providing means in response to said second electrical output signal.

2. The mechanism of claim 1, further comprising means for providing a predetermined reference pressure, and wherein said pressure-sensitive means comprises:
    a chamber fluidly communicating with said passageway;
    a resilient diaphragm dividing said chamber into first and second compartments, said first compartment communicating with said passageway and subject to said patient-induced respiratory pressures, said second compartment being subject to said reference pressure, said diaphragm providing said high velocity, low volume flow of gas in response to a patient-induced pressure differential between said first and second compartments; and
    means for communicating said reference pressure to said second compartment.

3. The mechanism of claim 2, wherein said diaphragm has sufficient sensitivity to provide said flow of gas in response to a slight pressure differential between said first and second compartments induced by the initiation of a respiratory effort by said patient.

4. The mechanism of claim 1, wherein said fluid flow sensing means includes temperature-sensitive means for producing said first and second electrical output signals, respectively, in response to first and second temperature changes, respectively, induced by said flow of gas in said first and second directions.

5. The mechanism of claim 3, wherein said temperature-sensitive means includes a thermistor.

6. The mechanism of claim 5, wherein said temperature sensitive means comprises:
    at least one thermistor; and
    heating means situated in said sensing tube in relation to said thermistor so as to produce said first and second temperature changes, respectively, in response to said flow of gas in said first and second directions.

7. The mechanism of claim 6, wherein said temperature-sensitive means comprises at least two thermistors, and wherein said heating means produces first and second temperature relationships between said thermistors, respectively, in response to said flow of gas in said first and second directions, said first temperature relationship producing said first electrical output signal and said second temperature relationship producing said second electrical output signal.

8. The mechanism of claim 1, wherein said control means comprises:
    discriminating means, responsive to said first and second electrical output signals from said fluid flow sensing means, for producing a triggering signal having an enabling value in response to said first output signal and a blocking value in response to said second output signal;
    means for generating a breathing rate signal;
    first switching means for producing a first pulse in response to said breathing rate signal;
    gating means, enabled by said first pulse, for transmitting a second pulse in response to said triggering signal only while said triggering signal has an enabling value;
    means for generating a command signal in response to said second pulse; and
    second switching means for actuating said assist cycle providing means in response to said command signal.

9. The mechanism of claim 8, further comprising:

resetting means for deactuating said first switching means in response to said command signal to enable a reactuation of said first switching means in response to a subsequent breathing rate signal.

10. The mechanism of claim 8, wherein said discriminating means comprises:
amplifier means, responsive to said first and second electrical output signals, and producing an amplifier output signal having a value greater than a first predetermined value in response to said first output signal, and a value less than said first predetermined value in response to said second output signal;
means for generating a threshold signal having a second predetermined value; and
comparator means, responsive to said amplifier output signal and to said threshold signal, for providing said triggering signal at said enabling value when the value of said amplifier output signal is at least approximately equal to the value of said threshold signal, and for providing said triggering signal at said blocking value when the value of said amplifier output signal is less than approximately the value of said threshold signal.

11. In a respiratory ventilator, of the type having means for providing a predetermined respiratory reference pressure and means for providing a respiration assist cycle for a patient, a mechanism for controlling said assist cycle providing means, comprising:
a housing having a chamber with first and second compartments;
a restricted-diameter sensing tube adapted to communicate a patient-induced respiratory pressure to said first compartment;
means for fluidly communicating said reference pressure to said second compartment;
diaphragm means, in said chamber, for (a) dividing said chamber into said first and second compartments, and (b) providing a high-velocity, low volume flow of gas through said sensing tube in response to a patient-induced pressure differential between said first and second compartments, said flow of gas being in a first direction in response to an inhalation-induced pressure differential and in a second direction in response to an exhalation-induced pressure differential, the velocity and volume of said flow of gas being determined, at least substantially in part, by the restricted diameter of said sensing tube;
temperature sensitive means in said sensing tube for producing variable electrical output signals in response to temperature changes in said sensing tube;
heating means located in said sensing tube substantially adjacent to said temperature sensitive means for providing a reference temperature and producing first and second temperature in said sensing tube around said temperature sensitive means and thereby, producing first and second electrical signals, respectively, in response to the flow of gas in said first and second directions past said temperature sensitive means and heating means;
discriminating means receiving said first and second electrical output signals and producing a triggering signal having a first value in response to said first electrical output signal and a second value in response to said second electrical output signal; and
control means, receiving said triggering signal, for actuating said assist cycle providing means in response to said first value of said triggering signal, and for blocking the actuation of said assist cycle providing means in response to said second value of said triggering signal.

12. The mechanism of claim 11, wherein said diaphragm means includes a resilient diaphragm of sufficient sensitivity to provide said flow of gas in response to a slight pressure differential between said first and second compartments induced by the initiation of a respiratory effort by said patient, and wherein the respective dimensions of said chamber and said sensing tube contribute to the low volume and high velocity of said flow of gas.

13. The mechanism of claim 11, wherein said temperature sensitive means includes a thermistor, and said heating means is located so that only gas flowing in said first direction cools said thermistor to produce said first electrical output signal.

14. The mechanism of claim 11, wherein said temperature sensitive means includes first and second thermistors, and said heating means is located so that gas flowing in said first direction cools said first thermistor relative to said second thermistor to produce said first electrical output signal, and gas flowing in said second direction cools said second thermistor relative to said first thermistor to produce said second electrical output signal.

15. The mechanism of claim 11, wherein said discriminating means comprises:
amplifier means, receptive to said first and second electrical output signals, for producing an amplifier output signal having a value greater than a first predetermined value in response to said first electrical output signal, and a value less than said first predetermined value in response to said second electrical output signal; and
comparator means, responsive to said amplifier output signal, for producing said triggering signal having said first value only when said amplifier output signal is at least approximately equal to a second predetermined value greater than said first predetermined value, and for producing said triggering signal having said second value when said amplifier output signal is less than approximately said second predetermined value.

16. In a respiratory ventilator of the type having means for providing a respiratory assist cycle for a patient, and means for providing a predetermined respiratory reference pressure, a mechanism for controlling said assist cycle providing means, comprising:
breathing conduit means adapted for fluid communication with the breathing passages of said patient;
a first conduit fluidly communicating with said breathing conduit means and receptive to patient-induced inhalation and exhalation pressures therein;
a second conduit receptive to said reference pressure;
a restricted diameter sensing tube having a first end in fluid communication with said first conduit;
pressure-sensitive means, coupled between a second end of said sensing tube and said second conduit, for producing a high velocity, low volume flow of gas through said sensing tube in a first direction in response to a first patient-induced pressure differential between said first and second conduits of a value representing the initiation of an inhalation effort by said patient, and in a second direction in response to a second patient-induced pressure differential between said first and second conduits representing the initiation of an exhalation effort by said patient, the velocity and volume of said flow of gas being determined, at least substantially in part, by the restricted diameter of said sensing tube;

fluid flow responsive means in said sensing tube for producing a first output signal having a first predetermined output level in response to gas flow in said first direction and a second output signal having a second predetermined output level different from said first predetermined output level in response to gas flow in said second direction;

discriminating means, receptive to said first and second output signals, for producing an enabling signal in response to said first output signal and a blocking signal in response to said second output signal;

control means for actuating said assist cycle providing means in response to said enabling signal, and for blocking the actuation of said assist cycle providing means in response to said blocking signal.

17. The mechanism of claim 16, wherein said pressure sensitive means includes a resilient diaphragm having a first side receptive to said patient-induced pressures through said sensing tube, and a second side receptive to said reference pressure through said second conduit.

18. The mechanism of claim 16, wherein said fluid flow responsive means comprises:

temperature sensitive means for providing output signals in response to temperature changes; and heating means for providing first and second temperature changes, respectively, in response to gas flow in said first and second directions, said temperature sensitive means thereby providing said first and second output signals, respectively, in response to said first and second temperature changes.

19. The mechanism of claim 18, wherein said temperature-sensitive means is a first thermistor and said heating means is a second thermistor heated by a constant current source.

20. The mechanism of claim 18, wherein said temperature-sensitive means includes at least one thermistor, and said heating means comprises a separate heating element.

21. The mechanism of claim 18, wherein said temperature-sensitive means comprises first and second thermistors, and said heating means includes means for supplying said first and second thermistors with a source of constant current.

22. The mechanism of claim 16, wherein said discriminating means comprises:

means for producing an intermediate signal in response to said first and second output signals, said intermediate signal having magnitude greater than a first predetermined value in response to said first output signal and less than said first predetermined value in response to said second output signal; and comparator means, responsive to said intermediate signal, for producing said enabling signal only when the magnitude of said intermediate signal is at least approximately equal to a second predetermined value greater than said first predetermined value.

23. The mechanism of claim 22, wherein said comparator means produces said blocking signal when the magnitude of said intermediate signal is less than approximately said second predetermined value, the input of said blocking signal to said actuation means preventing the actuation of said assist cycle providing means.

* * * * *